US012624062B2

(12) United States Patent
Yang et al.

(10) Patent No.: US 12,624,062 B2
(45) Date of Patent: May 12, 2026

(54) METHOD FOR MANUFACTURING ALLULOSE

(71) Applicant: SAMYANG CORPORATION, Seoul (KR)

(72) Inventors: Jae-Kyung Yang, Suwon-si (KR); Ji Won Park, Seongnam-si (KR); Jung Sook Han, Anyang-si (KR); Go-Eun Kim, Gwangju-si (KR); Choong Woo Nam, Seoul (KR); Chong Jin Park, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 688 days.

(21) Appl. No.: 17/772,651

(22) PCT Filed: Oct. 29, 2020

(86) PCT No.: PCT/KR2020/014966
§ 371 (c)(1),
(2) Date: Apr. 28, 2022

(87) PCT Pub. No.: WO2021/086086
PCT Pub. Date: May 6, 2021

(65) Prior Publication Data
US 2022/0380400 A1 Dec. 1, 2022

(30) Foreign Application Priority Data

Oct. 31, 2019 (KR) ........................ 10-2019-0137593
Aug. 13, 2020 (KR) ........................ 10-2020-0101994

(51) Int. Cl.
C07H 3/02 (2006.01)
B01D 15/18 (2006.01)
B01D 15/36 (2006.01)

(52) U.S. Cl.
CPC ........... *C07H 3/02* (2013.01); *B01D 15/1821* (2013.01); *B01D 15/361* (2013.01)

(58) Field of Classification Search
CPC .... C07H 3/02; B01D 15/1821; B01D 15/361; B01D 15/362; C12P 19/24; C12P 19/14; C12P 19/02; C12Y 302/01026
See application file for complete search history.

(56) References Cited

U.S. PATENT DOCUMENTS 2,985,589 A 5/1961 Broughton et al.
11,358,980 B2 * 6/2022 Park ........................ C07H 1/06
(Continued)

FOREIGN PATENT DOCUMENTS

CN 1914329 2/2007
CN 103333935 10/2013
(Continued)

OTHER PUBLICATIONS

Valdes Delgado, A., Armas Casanova, C. d. (2001). Sugar Processing and By-products of the Sugar Industry. Italy: Food and Agriculture Organization of the United Nations. Available at: https://www.google.com/books/edition/_/EJywqC8rJ6QC?hl=en&gbpv=0 (Year: 2001).*

(Continued)

*Primary Examiner* — Thomas J. Visone
(74) *Attorney, Agent, or Firm* — LEX IP MEISTER, PLLC

(57) ABSTRACT

The present disclosure relates to an improved method for producing allulose and, more particularly, to a method for preparing a fructose-containing raw material solution by using raw sugar as a raw substrate used in the production process.

13 Claims, 3 Drawing Sheets

(56) References Cited

U.S. PATENT DOCUMENTS

| | | | |
|---|---|---|---|
| 2019/0000116 A1 | 1/2019 | Pandey et al. | |
| 2020/0377540 A1* | 12/2020 | Park | B01D 15/361 |

FOREIGN PATENT DOCUMENTS

| | | | | |
|---|---|---|---|---|
| CN | 104769125 | 7/2015 | | |
| CN | 105331751 | 2/2016 | | |
| CN | 108588149 | 9/2018 | | |
| CN | 110072871 | 7/2019 | | |
| EP | 3553070 | 10/2019 | | |
| EP | 3553071 | 10/2019 | | |
| IN | 201711006155 | 8/2018 | | |
| JP | 2014-140347 | 8/2014 | | |
| JP | 2018-506292 | 3/2018 | | |
| JP | 2019-500050 | 1/2019 | | |
| KR | 10-2009-0116283 | 11/2009 | | |
| KR | 10-2009-0116770 | 11/2009 | | |
| KR | 10-1318422 | 10/2013 | | |
| KR | 10-2014-0021974 | 2/2014 | | |
| KR | 10-2014-0054997 | 5/2014 | | |
| KR | 10-2014-0080282 | 6/2014 | | |
| KR | 20180065782 A | * 12/2016 | | B01D 15/185 |
| KR | 10-1723007 | 4/2017 | | |
| KR | 10-2017-0057078 | 5/2017 | | |
| KR | 10-2017-0118777 | 10/2017 | | |
| KR | 10-2018-0035413 | 4/2018 | | |
| KR | 10-2018-0065782 | 6/2018 | | |
| KR | 10-2018-0076028 | 7/2018 | | |
| KR | 10-2019-0098040 | 8/2019 | | |
| WO | 2014-168018 | 10/2014 | | |
| WO | 2018-105934 | 6/2018 | | |
| WO | WO-2018105934 A2 | * 6/2018 | | B01D 15/18 |
| WO | 2019-156483 | 8/2019 | | |

OTHER PUBLICATIONS

Kulshrestha, Samarth & Tyagi, Prasidhi & Sindhi, Vinita & Yadavilli, Kameshwar. (2013). Invertase and its applications—A brief review. Journal of Pharmacy Research. 7. 10.1016/j.jopr.2013.07.014. (Year: 2013).*

EPO, The supplementary partial European Search Report of the corresponding European Patent Application No. 20882296.5 dated Nov. 13, 2023.

KIPO, PCT Search Report & Written Opinion of PCT/KR2020/014966 dated Jan. 29, 2021.

KIPO, Office Action of the corresponding Korean Patent Application No. 10-2020-0101994 dated Sep. 22, 2022.

Li Kai et al., "Process Optimization of Producing Fructose Syrup by Raw Sugar Hydrolysis", China Condiment, vol. 44, issue 5, May 2019.

J. A. Solis-Fuentes et al., "Direct Sucrose Hydrolysis in Sugarcane Juice with Immobilized Invertase: Multi-response Optimization Using Desirability Function on Conversion and Reactor Volumetric Productivity," Sugar Tech, vol. 17, No. 3, pp. 266-275, Aug. 2014, doi: https://doi.org/10.1007/s12355-014-0320-7.

IP Australia, Office Action of AU 2020375503 dated Feb. 8, 2024.

Jucimara K. de Andrade et al., "In House Validation from Direct Determination of 5-Hydroxymethyl-2-furfural (HMF) in Brazilian Corn and Cane Syrups Samples by HPLC-UV", Food Chemistry. Jan. 1, 2016;190:481-6.

SIPO, Office Action of CN 202080082878.8 dated Mar. 16, 2024.

Dong Renwei, "Starch Deep Processing Technology", Sichuan Science and Technology Press, p. 166, Aug. 31, 1991.

IP Australia, Office Action of AU 2020375503 dated May 17, 2023.

Yang, J., Tian, C., Zhang, T., Ren, C., Zhu, Y., Zeng, Y., Men, Y., Sun, Y. and Ma, Y., 2019. Development of food-grade expression system for D-allulose 3-epimerase preparation with tandem isoenzyme genes in Corynebacterium glutamicum and its application in conversion of cane molasses to D-allulose. Biotechnology and Bioengineering, 116 (4), pp. 745-756.

JPO, Office Action of JP 2022-525222 dated Jun. 27, 2023.

* cited by examiner

FIG. 3

| Height | 4.4 | 4.6 | 5 | 5.2 | 5.4 | 6.3 | RT 6.5 | 7 | 7.3 | 7.5 | 7.8 | 9.8 | 10+ |
|---|---|---|---|---|---|---|---|---|---|---|---|---|---|
| Raw sugar / Sugar | | 0.1 | | | | 0.4 | | 0.4 | 0.3 | 0.6 | 0.1 | | 0.3 |
| Mother liquor 1 | | | | | | | 0.1 | | | 0.1 | 2 | | |
| Mother liquor 2 | 0.4 | 0.2 | | | 0.2 | 0.5 | | 0.9 | 0.3 | 0.4 | 0.8 | | |
| Mother liquor 3 | 1.9 | 0.7 | 0.9 | 1 | 1.2 | 1.6 | 1 | 1.4 | 0.7 | 0.9 | 2.4 | | 1.81 |
| Mother liquor 4 | 2.7 | 1 | 1.1 | 1.2 | 1.6 | 2.5 | 1.5 | 3.1 | 1.2 | 1.5 | 4.8 | | |
| Residuals | 10.3 | 6.9 | 1.3 | | 3.5 | | 0.9 | | | 3.3 | 2.9 | 1.1 | 18.92 |

METHOD FOR MANUFACTURING ALLULOSE

TECHNICAL FIELD

The present disclosure relates improved method for producing allulose and, more particularly, to a method for preparing a fructose-containing raw material solution by using raw sugar as a raw substrate used in the production process.

BACKGROUND ART

Allulose is an epimer of fructose(D-fructose) and is one kind of functional saccharides known as a rare saccharide, and it has been known to have an efficacy on prevention and improvement of diabetes, since it has sweetness of about 60 to 70% of sugar and almost zero calorie. In addition, allulose is known to have excellent solubility, and it is one of materials where utilization for food is attracting attention.

Allulose is one of popular sugars that can replace sugar or fructose as a functional sweetener. Allulose can be produced by chemical or biological methods, The fructose-containing solution, which is a reaction raw material used in the allulose conversion step, may be a fructose isomerized product obtained by converting glucose obtained from decomposition of starch or the like by an isomerization reaction, or a fructose isomerized product obtained by hydrolyzing sugar. When allulose is produced using a sugar raw material, a process of producing sugar from existing raw sugar is required, and there are problems such as an increase in production cost and yield, and addition of multiple processes in the sugar production process. Further, in the case of isomerized sugar syrup obtained from existing corn, it contains a substance of DP3 or higher, which causes a problem of affecting the separation ability.

When allulose is produced using sugar raw materials, the process of producing sugar from raw sugar can be eliminated. In the case of isomerized sugar syrup obtained from corn, substances of DP3 or higher also exist, which may affect the decomposition ability. Further, recently, due to price competition with overseas manufacturers of glucose and fructose corn syrup and other sugar cane sources, raw material costs are putting a burden on manufacturing costs. Thus, there is a need to produce allulose with cheaper raw materials and processes.

In the allulose production process, the allulose conversion product has a low allulose content, and so it is necessary to increase the allulose purity for commercialization or crystallization. For this purpose, purification and concentration steps are required. Additionally, allulose has a demand for a crystalline powder, but allulose has low crystallinity which makes it difficult to crystallize. Further, when the allulose concentrate or allulose crystallization solution contains impurities, impurities need to be removed to ensure product quality. Particularly, some impurities may interfere with allulose crystallization or crystal growth.

Therefore, there is an urgent need to provide an efficient allulose production process with cheaper raw materials and processes, and to develop an allulose production method that minimizes the content of impurities contained in the allulose solution or the generation of impurities in the allulose production process.

DETAILED DESCRIPTION OF THE INVENTION

Technical Problem

An object of the present disclosure is to provide a method of producing allulose in which a fructose-containing raw material prepared using a raw material for sugar production is put as a raw material for the allulose production process, in order to improve the purity and yield of allulose by using sugar raw materials and to increase the utilization rate of raw materials, and a device used therefor.

Another object of the present disclosure is to provide a method of producing allulose composes putting, as a raw material for the allulose production process, a fructose-containing raw material prepared using raw sugar, which can eliminate a sugar production process and a glucose production process so as to simplify the production process, as compared with a conventional method of producing allulose using sugar or isomerized fructose obtained from starch, and which can utilize low-cost raw materials and thus reduce production cost, as a raw material for the allulose production process, and a device used therefor.

Yet another object of the present disclosure is to provide a method of producing allulose comprises putting, as a raw material for the allulose, production process, a fructose-containing raw material prepared using raw sugar, which can control the content of impurities contained in allulose syrup or powder by reducing the content of oligosaccharides having DP3 or higher and other impurities contained in isomerized sugar syrup using a conventional starch in a conventional method, and a device used therefor.

Technical Solution

According to the present disclosure, there is provided a method of producing a fructose-containing raw material, comprising putting an invert sugar produced from raw sugar into a fructose separation process, in order to improve allulose purity and yield, and reduce impurities contained in the produced allulose by applying a high-purity fructose produced directly from raw materials for sugar production, as a raw material for allulose production, and a device used therefor.

The biological production method of allulose includes the steps of preparing allulose with a fructose epimer conversion reaction, separating and purifying it. The fructose or fructose-containing raw material as a raw material for producing allulose, is prepared by the method comprising producing glucose by decomposition of starch, producing fructose by isomerization of glucose, and separating and purifying fructose in the case of conventional starch-derived fructose. In the case of sugar-derived fructose, the method comprises steps of separating and purifying sugar from raw materials for sugar production such as raw sugar, producing glucose and fructose by decomposition of sugar, and separating and purifying fructose. That is, the direct raw material for starch-derived fructose is a starch-derived isomerized sugar containing glucose, and the direct raw material for sugar-derived fructose is sugar separated, purified and crystallized from raw materials for sugar production such as raw sugar. Thus, pre-steps for preparing a raw material for fructose production are essential.

Therefore, in the case of conventional starch-derived fructose or sugar-derived fructose, fructose cannot be directly produced from the initial raw material of the process, and as a raw material for fructose production, the starch-derived fructose is prepared by the method including a glucose production step and a sugar-derived fructose is prepared by the method further including a sugar decomposition process. That is, since at least a two-step process must be performed, there are problems that the process is complicated, the process yield is lowered, and by-products are generated in each process.

Further, the starch-derived fructose contains many impurities of saccharides having DP3 or higher in the glucose production process which is a pre-stage reaction of the fructose production process, and thus it makes the separation and purification of fructose be difficult. When allulose is produced using starch-derived fructose, the allulose conversion product may also contain impurities of saccharides having DP3 or higher, and thus it makes the separation and purification steps of allulose be difficult and complicated. The sugar purification step, which is a pre-step reaction for producing sugar-derived fructose, for example, a number of steps for removing by-products are required in the process of dissolving raw sugar and crystallizing it into sugar.

Therefore, the raw material for producing fructose according to the present disclosure does not include a separate process for preparing sugar or isomerized sugar, and can make it possible to perform a process of directly treating invertase with a raw material for sugar production, for example, a juice or concentrate of sugar cane or sugar beet, or a solution dissolved with sugar crystals obtained by removing molasses from the juice or concentrate, and to separate and purify fructose. Thus, a pre-reaction for preparing raw materials for fructose production is not required, so as to simplify the process.

Allulose is unstable as the pH is lower and the temperature is higher. Thus, the content of allulose is changed in the actual production process, especially in the concentration step. Such problems reduce the purity of high-purity allulose, thereby greatly affecting the crystallization step. Actually, it is found that while the content of allulose is reduced in this process, the content of product (impurity) converted from allulose as by-product increases, and the component acts as an inhibitor in the growth of allulose crystal particles. This greatly affects the particle size and yield of the crystal particle. Thus, the present disclosure controls the impurities other than allulose in the allulose production process, and thus can improve the shape, structure and size of allulose crystal particles, crystal purity, crystal formation rate, and crystal yield. The impurity may be an allulose-modified product, an allulose-modified polymer, or an intermediate material produced and converted in the process of allulose decomposition, and includes hydroxymethylfurfural (HMF), more preferably 5-HMF.

According to the present disclosure, the production, separation and/or purification of allulose is performed under conditions in which the impurities, for example, 5-HMF contained in the allulose conversion product are not produced or are producted minimally, so that the content of impurities contained in allulose syrup can be reduced. Thus, it reduces the impurity content of the crystallization raw solution, and lower the content of impurities that interfere with crystal growth, thereby improving crystal shape and crystal yield.

When high-purity fructose is directly produced using raw materials for sugar production according to the present disclosure, and is used for producing allulose, fructose-containing raw materials as raw materials for the allulose conversion reaction may contains the impurities in an amount of be 0.001 to 2.2 mg/L, for example, 2.2 mg/L or less, 2.1 mg/L or less, 2.0 mg/L or less, 1.9 mg/L or less, 1.8 mg/L or less, 1.7 mg/L or less, 1.6 mg/L or less, 1.5 mg/L or less, 1.4 mg/L or less, 1.3 mg/L or less, 1.2 mg/L or less, 1.1 mg/L or less, 1.0 mg/L or less, 0.9 mg/L or less, 0.8 mg/L or less, 0.7 mg/L or less, 0.6 mg/L or less. Specifically, the fructose-containing raw material may have a solid content of 45 to 55 wt %.

After the product of allulose conversion reaction is subjected to high-purity separation using SMB and ion purification processes, the obtained allulose syrup may have a 5-HMF content of 0.001 to 5.7 mg/L, for example, 5.7 mg/L or less, 5.6 mg/L or less, 5.5. mg/L or less, 5.25 mg/L or less, 5.0 mg/L or less, 4.7 mg/L or less, 4.5 mg/L or less, 4.25 mg/L or less, 4.0 mg/L or less, 3.7 mg/L or less, 3.5 mg/L or less, 3.25 mg/L or less, 3.0 mg/L or less, 2.7 mg/L or less, 2.5 mg/L or less, 2.25 mg/L or less, 2.0 mg/L or less, 1.7 mg/L or less, 1.5 mg/L or less, or 1.25 mg/L or less. Specifically, the fructose-containing raw material may have a solid content of 70 to 75 wt %.

Based on 100 wt % of the total solid content in allulose, hydroxymethylfurfural may be contained in an amount of 0.01 wt % or less, 0.05 wt % or less, 0.06 wt % or less, 0.07 wt % or less, 0.08 wt % or less, 0.085 wt % or less, 0.09 wt % or less, or 0.095 wt % or less, or, for example, it may not be contained. The hydroxymethylfurfural may be 5-hydroxymethylfurfural.

When allulose is produced as a raw material for sugar production, the enzyme reaction, decolorization, filtration, and purification are directly performed, without the need to proceed with the conventional process of producing starch-derived isomerized sugar syrup or sugar decomposition products, thereby reducing product loss and unnecessary processes in the conventional process. The starch-derived isomerized sugar is lowered in the separating ability due to substances having DP3 or higher contained in the raw material, compared to fructose-containing substrate derived from raw sugar. A sugar decomposition product has the advantage of eliminating unnecessary processes proceeding in sugar production.

An embodiment of the present disclosure relates to a method for producing allulose, the method comprising the steps of: preparing a fructose-containing raw material by obtaining an invert sugar syrup containing fructose and glucose using a raw material for sugar production containing sugar and an invertase, and putting it into a fructose separation process to prepare a fructose-containing raw material, and performing an allulose conversion reaction using the fructose-containing raw material. The production method does not include a step of isomerizing starch-derived glucose, or separating or purifying sugar from a raw material for sugar production.

The fructose separation step comprises at least one selected from the group consisting of an activated carbon treatment step, an ion purification step, a high-purity separation step using simulated moving bed (SMB) chromatography, and a concentration step for the invert sugar syrup. For example, the fructose separation step may include an ion purification step, a high-purity separation step using simulated moving bed (SMB) chromatography, and a concentration step for the invert sugar syrup.

The invert sugar syrup may include fructose, glucose, and saccharides including disaccharide or higher saccharide. In an embodiment of the present disclosure, the fructose-containing raw material prepared from the raw material for sugar production may have an oligosaccharide content of DP3 or higher of 2.0 wt % or less, based on the saccharide solid content. The invert sugar syrup may have a saccharide solid content of 10 wt % or more. In addition, a fructose-containing raw material having a fructose content of 90 wt % or more may be prepared through a fructose separation process, based on the total saccharide solid content of the fructose-containing raw material.

Based on the total saccharide solid content of the invert sugar syrup, the total content of fructose and glucose may be 90 wt % or more. Specifically, based on 100 wt % of the total solid content of fructose and glucose contained in the invert sugar syrup, the fructose may be included in an amount of 40 wt % or more and the glucose is included in an amount of 60 wt % or less.

The fructose-containing raw material obtained by the above production method may contain 0.001 to 2.2 mg/L of 5-HMF, and the allulose conversion product may contain 0.001 to 5.7 mg/L of 5-HMF.

The allulose conversion product may be obtained by treating a fructose-containing raw material with a biological allulose conversion step. The fructose content of the fructose-containing raw material subjected to an allulose conversion reaction may be 85 wt % or more based on 100 wt % of the total saccharide solid content.

Another embodiment of the present disclosure relates to an allulose-containing composition comprising 1.0 wt % or less of 5-HMF, where allulose may contain in an amount of 5 wt % or more based on the solid content, and the content of oligosaccharides having DP3 or higher is 2.0 wt % or less, 1.5 wt % or less, 1.0 wt % or less, 0.5 wt % or less, 0.1 wt % or less, 0.05 wt % or less, 0.01 wt % or less, 0.005 wt % or less, 0.001 wt % or less, or 0.0001 wt % or less based on the solid content, and preferably, it may not be included.

Hereinafter, the present disclosure will be described in more detail.

The method for producing allulose using raw sugar according to the present disclosure includes the step of producing a fructose-containing product using a raw material for sugar production.

The step of producing a fructose-containing product using the raw material for sugar production is the step of contacting the raw sugar with an invertase to hydrolyze sugar contained in the raw sugar and convert it into a mixture of glucose and fructose, so as to produce a fructose-containing product, for example, invert syrup. The sugar is completely hydrolyzed to glucose and fructose to prepare an invert syrup containing fructose and glucose, in order that the saccharides having DP2 or higher is low, for example 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, or 0.5 wt % or less, based on 100 wt % of the total saccharide solid content.

More specifically, in the process of producing fructose according to an embodiment of the present disclosure, fructose can be obtained from raw sugar including sugar. Thereby, an allulose production method can be provided to produce high-yield allulose by using raw sugar instead of the separated and purified raw materials such as glucose, fructose, and sugar, and does not contain impurities, e.g., 5-HMF, thereby enabling mass production of allulose in high yield at very low cost.

The inverting step can be performed by the step of contacting raw sugar with a biocatalyst including an enzyme that decomposes sugar into glucose and fructose, a microorganism producing the enzyme (e.g., including microbial cells, lysates of the microbial cells, microbial cultures, and supernatant of the microbial cultures), such as a step of mixing the biocatalyst with the raw sugar or a step of contacting the raw sugar with a support on which the biocatalyst is immobilized.

Specifically, the raw material solution for sugar production is put in a reaction tank and added with water to prepare an invertase-treated raw material with a solid content of 30 wt % or more, for example, 35 to 45 wt %, preferably 40 wt %, the invertase-treated raw material is adjusted to a temperature of 55 to 75° C., preferably 60° C. and the pH to 4.0 to 5.5, preferably pH 4.5 by adding hydrochloric acid, and then the invertase is added in an amount of 0.01 to 5.0 wt %, for example, 0.01% to 1 wt % based on the solid content, to carry out hydrolysis for 16 to 48 hours or 20 to 28 hours.

The invertase can be used without limitation as long as it is an enzyme that decomposes sugar into glucose and fructose, and examples thereof may be sumizyme INV-L (HBI ENZYME INC), but is not limited thereto.

In the present disclosure, a raw material for preparing a fructose-containing raw material for the allulose conversion reaction is a raw material for sugar production, and includes a juice or concentrate of sugar cane or sugar beet, or a crystal obtained by removing molasses from the juice or concentrate. The invert sugar means the products that sugar contained in a raw material for sugar production, for example, raw sugar is decomposed to glucose and fructose, by acid hydrolysis of raw sugar at high temperature or enzymatic hydrolysis with treatment of invertase. The starting material of the present disclosure is preferably the juice or squeezed liquid (e.g., extracted without processing) of sugar cane or sugar beet obtained by pressing them.

The raw sugar applicable to the present disclosure can be a commercially available product, or a juice obtained by squeezing sugar cane or sugar beet or additional-processed juice. For example, in the step of preparing sugar cane juice, the juice is prepared by cutting sugar cane stems as it is, and removing the impurities by adding lime to the juice to filter out impurities and increase the pH so that proteins, fats, and suspended matter are precipitated to remove impurities. The step of heating and concentrating the juice from which the impurities have been removed can be further performed, and crystals can be obtained by centrifuging and separating crystals and molasses.

For example, sugar cane can be squeezed to obtain sugar cane juice, and the juice can be filtered to remove impurities, and optionally, a concentration step may be performed. It is sufficient to treat only the step of removing not only solids but also soluble substances, which can contaminate the enzyme and reduce its efficiency. Before performing the enzyme conversion step, the prepared invert syrup can be further concentrated to a solid content of 68 wt % in order to inhibit the growth of microorganisms and reduce transportation costs.

The sugar cane juice has a saccharide content of about 16 to 23 wt %, in which 90 wt % or more of the saccharides is sucrose. The raw material to be treated with the invertase may be a raw sugar solution having a solid content of 35 to 65 wt %, for example, 45 to 60 wt % (or brix).

The hydrolyzed invert syrup or the fructose-containing product produced by the invertase treatment may have a saccharide solid content of 10 wt % or more, 15 wt % or more, 20 wt % or more , 25 wt % or more , 30 wt % or more, 35 wt % or more, 40 wt % or more, 45 wt % or more, 50 wt % or more, or 55 wt % or more, for example, 30 to 80 wt %, 35 wt % to 80 wt %, 40 wt % to 80 wt %, 45 wt % to 80 wt %, 50 wt % to 80 wt %, 55 wt % to 80 wt %, 30 to 75 wt %, 35 wt % to 75 wt %, 40 wt % to 75 wt %, 45 wt % to 75 wt %, 50 wt % to 75 wt %, 55 wt % to 75 wt %, 30 to 70 wt %, 35 wt % to 70 wt %, 40 wt % to 70 wt %, 45 wt % to 70 wt %, 50 wt % to 70 wt %, 55 wt % to 70 wt %, 30 to 65 wt %, 35 wt % to 65 wt %, 40 wt % to 65 wt %, 45 wt % to 65 wt %, 50 wt % to 65 wt %, 55 wt % to 65 wt %, 30 to 60 wt %, 35 wt % to 60 wt %, 40 wt % to 60 wt %, 45 wt % to 60 wt %, 50 wt % to 60 wt %, or 55 wt % to 60 wt %.

The saccharide contained in the invertase-treated product includes fructose and glucose as the main components, and may include the remaining disaccharides or higher saccharides. The total content of fructose and glucose may be 90 wt % or more, 91 wt % or more, 92 wt % or more, 93 wt % or more, 94 wt % or more, 95 wt % or more, 96 wt % or more, 97 wt % or more, 98 wt % or more, 99 wt % or more or 99.5 wt % or more, based on 100 wt % of the total saccharide solid content. The content of saccharides other than glucose and fructose, such as di-or higher saccharides may be 10 wt % or less, 9 wt % or less, 8 wt % or less, 7 wt % or less, 6 wt % or less, 5 wt % or less, 4 wt % or less 3 wt % or less , 2 wt % or less, 1 wt % or less, or 0.5 wt % or less, for example, 0.5 to 1.0 wt % or less, based on 100 wt % of the total saccharide solid content.

The content of glucose and fructose contained in the invertase treatment product, is a weight ratio of 1:1, since the sugar contained in the raw material is decomposed by the action of the invertase to produce the same amount of glucose and fructose. Thus, it can be contained in an amount of 50 wt %, based on 100 wt % of the total content of fructose and glucose. Alternatively, depending on the contents of glucose and fructose in the raw sugar before processing the invertase, the glucose and fructose contents in the final inversion product can be determined by adding the same amount of glucose and fructose content obtained by decomposition of sugar according to the content of glucose and fructose in the raw sugar before processing the invertase, the glucose and fructose contents contained in the final inverting product can be determined by adding the same amount of glucose and fructose content obtained from sugar decomposition. Therefore, based on 100 wt % of the total content of glucose and fructose, the contents of fructose contained in the invertase treatment product may be 40 wt % or more, 42.5 wt % or more, 45 wt % or more, 46 wt % or more, 47 wt % or more, 47.5 wt % or more, 48 wt % or more, 48.5 wt % or more, 49 wt % or more, 49.5 wt % or more, 50 wt % or more, 51 wt % or more, 52 wt % or more, 53 wt % or more, 54 wt % or more, 55 wt % or more, 56 wt % or more, 57 wt % or more, 58 wt % or more, or 59 wt % or more, for example, 40 to 60 wt %, 42.5 to 60 wt %, 45 to 60 wt %, 46 to 60 wt %, 47 to 60 wt %, 47.5 to 60 wt %, 48 to 60 wt %, 48.5 to 60 wt %, 49 to 60 wt %, 49.5 to 60 wt %, 50 to 60 wt %, 51 to 60 wt %, 52 to 60 wt %, 53 to 60 wt %, 54 to 60 wt %, 55 to 60 wt %, 56 to 60 wt %, 57 to 60 wt %, 58 to 60 wt %, 59 wt % to 60 wt %, 40 to 55 wt %, 42.5 to 55 wt %, 45 to 55 wt %, 46 to 55 wt %, 47 to 55 wt %, 47.5 to 55 wt %, 48 to 55 wt %, 48.5 to 55 wt %, 49 to 55 wt %, 49.5 to 55 wt %, 50 to 55 wt %, 51 to 55 wt %, 52 to 55 wt %, 53 to 55 wt %, 54 to 55 wt %, 40 to 54 wt %, 42.5 to 54 wt %, 45 to 54 wt %, 46 to 54 wt %, 47 to 54 wt %, 47.5 to 54 wt %, 48 to 54 wt %, 48.5 to 54 wt %, 49 to 54 wt %, 49.5 to 54 wt %, 50 to 54 wt %, 51 to 54 wt %, 52 to 54 wt %, 53 to 54 wt %, 40 to 53 wt %, 42.5 to 53 wt %, 45 to 53 wt %, 46 to 53 wt %, 47 to 53 wt %, 47.5 to 53 wt %, 48 to 53 wt %, 48.5 to 53 wt %, 49 to 53 wt %, 49.5 to 53 wt %, 50 to 53 wt %, 51 to 53 wt %, 52 to 53 wt %, 40 to 52 wt %, 42.5 to 52 wt %, 45 to 52 wt %, 46 to 52 wt %, 47 to 52 wt %, 47.5 to 52 wt %, 48 to 52 wt %, 48.5 to 52 wt %, 49 to 52 wt %, 49.5 to 52 wt %, 50 to 52 wt %, 51 to 52 wt %, 40 to 51 wt %, 42.5 to 51 wt %, 45 to 51 wt %, 46 to 51 wt %, 47 to 51 wt %, 47.5 to 51 wt %, 48 to 51 wt %, 48.5 to 51 wt %, 49 to 51 wt %, 49.5 to 51 wt %, 50 to 51 wt %, 40 to 50 wt %, 42.5 to 50 wt %, 45 to 50 wt %, 46 to 50 wt %, 47 to 50 wt %, 47.5 to 50 wt %, 48 to 50 wt %, 48.5 to 50 wt %, 49 to 50 wt %, 49.5 to 50 wt %, 50 wt %, 40 to 49 wt %, 42.5 to 49 wt %, 45 to 49 wt %, 46 to 49 wt %, 47 to 49 wt %, 47.5 to 49 wt %, 48 to 49 wt %, 48.5 to 49 wt %, 40 to 48.5 wt %, 42.5 to 48.5 wt %, 45 to 48.5 wt %, 46 to 48.5 wt %, 47 to 48.5 wt %, 47.5 to 48.5 wt %, 48 to 48.5 wt %, 40 to 48 wt %, 42.5 to 48 wt %, 45 to 48 wt %, 46 to 48 wt %, 47 to 48 wt %, 47.5 to 48 wt %, 40 to 47 wt %, 42.5 to 47 wt %, 45 to 47 wt %, 46 to 47 wt %, 40 to 46 wt %, 42.5 to 46 wt %, 45 to 46 wt %, 40 to 45 wt %, or 42.5 to 45 wt %. Based on 100 wt % of the total content of fructose and glucose, the glucose content may be the remaining amount of the fructose content (2) Step of Obtaining High-Purity Fructose from a Product Containing Fructose This is a step of enzymatically hydrolyzing a raw sugar solution having a solid content of 35 to 45 wt % using an invertase, and subjecting the obtained fructose and glucose mixture to a decolorization step, an ion purification step, and a concentration step to prepare a raw syrup containing 43 to 48 wt % of fructose.

In the decolorization step, the activated carbon is brought into contact with the reaction solution and reacted at a temperature of 40 to 50° C. for 0.5 to 5 hours, and then the reaction solution containing the activated carbon is subjected to a solid-liquid separation step to obtain a filtrate with removing the impurities as a filtration residue. The filtration can be performed using filtration device such as a filter press.

It can be selectively stirred in the activated carbon reaction step, and the stirring speed of the reaction solution may be 5 to 500 rpm, or preferably 50 to 300 rpm. The stirring speed may be appropriately selected in consideration of the degree of dispersion of the activated carbon and the cost required for stirring. The contact time between the activated carbon and the reaction solution can be appropriately selected in consideration of the degree of dispersion of the activated carbon and the removal efficiency of impurities, etc. and for example, it may be 0.5 to 5 hours, preferably 0.5 to 2 hours. If the contact time is short, the removal of impurities, such as decolorization, may not be sufficiently performed. If the contact time is long, the decomposition and browning of the main components may occur.

The activated carbon used in the activated carbon treatment step may be of coal-based or wood-based origin, and impurities can also be selectively removed according to the pore size of the activated carbon.

The ion purification step can be performed using at least one type of ion resin selected from the group consisting of a cation exchange resin, an anion exchange resin, and a resin in which a cation and an anion exchange resin are mixed, and the ion purification step of fructose can be applied similarly by the ion purification step of the allulose, inverting product.

in one embodiment, the method for preparing a fructose-containing raw material includes (1) an inverting step of treating raw sugar with an invertase to prepare a mixed solution containing glucose and fructose; (2) a step of preparing a fructose-containing raw material including a fructose separating process of ion purification and separation of the inverted product using simulated moving bed (SMB) chromatography to separate fructose fraction and raffinate.

As used herein, the term "raffinate" is also referred to as an extracting residue, and the product obtained when the raw material subjected the separation process passes through the separation step includes a target fraction containing a target substance whose content is to be increased by the separation process, and a residual liquid containing substances to be removed or reduced in content in the separation step, which is referred to a residual liquid raffinate.

The fructose-containing raw material, which is a substrate for the allulose conversion reaction, may perform a step of contacting raw sugar with an invertase to prepare an invert sugar syrup containing fructose and separating high-purity fructose from the invert sugar syrup.

The step of separating high-purity fructose from the invert sugar syrup may be first performed by at least one step selected from the group consisting of (A) an inverting step of preparing invert sugar syrup containing fructose using raw sugar and invert catalyst, (B) at least a step of performing a primary ion purification, a separation using SMB chromatography, and a secondary ion purification, which are a separation step for fructose production, for the invert sugar syrup, and additionally, activated carbon treatment and filtration treatment may be performed.

The fructose production process of the present disclosure may be used in both a continuous type and a batch type, and a continuous process may be used according to an embodiment, but is not limited thereto.

In an embodiment of the present disclosure, in order to separate and concentrate the reactant fructose, the reactant invert sugar obtained in step (A) may be subjected to a first ion purification and SMB chromatography separation step. The separation process for fructose production may be performed using the same method, process, and reaction conditions as the conventional separation process for fructose production. The primary ion purification and SMB chromatography are substantially the same as those described in the separation process of the allulose conversion product in (2) above.

The separation step for fructose production of the present disclosure may include primary ion purification, SMB chromatography separation, secondary ion purification and concentration steps, and optionally, the step of removing impurities from the fructose isomerization reactant, a desalting step, a decolorizing step, or a decolorizing and desalting step may be performed. The step of removing the impurities can be performed by flowing through a column filled with an ion exchange resin in order to remove impurities, such as colored components and ionic components, such as a step of removing insoluble substances using filtration, or a step of decoloring using activated carbon. A fructose syrup having a fructose content of 40 to 44 wt % is obtained through a step of removing impurities from the fructose isomerization product.

Then, a glucose raffinate and a fructose fraction are obtained using a simulated moving bed (SMB), and the fructose fraction can be subjected to a secondary ion purification and concentration step to obtain a fructose solution having a solid content of 45 to 55 wt % based on 100 wt % of the total solid content.

For the separation of glucose and fructose, it can be performed in substantially the same as the SMB chromatograph separation process used in the separation process of the allulose conversion product. For example, a calcium (Ca) type strong acidic cation resin having a particle size of 220 to 320 μm may be used. The high-purity separation step may be performed at a temperature of 40 to 60° C., for example, 60° C.

The fructose production process of the present disclosure can be used in both a continuous type and a batch type, and is preferably a continuous type. Hereinafter, the fructose production process including the recycle of the fructose raffinate according to the present disclosure will be described in detail for each step.

As the primary ion purification in order to remove impurities such as colored and ionic components, it can be carried out in the same or different method as the primary ion purification of allulose, and it can be carried out by using one or two or more separation columns filled with the same type or different types of ion exchange resins. The ion purification step may be performed by setting the process conditions in consideration of the physical properties of the resin used for ion purification and ion purification efficiency.

The step of removing the impurities can be performed by flowing through a column filled with an ion exchange resin in order to remove impurities, such as colored components and ionic components, such as a step of removing insoluble substances using filtration, a step of decoloring using activated carbon. For example, the fructose fraction obtained in the high-purity separation process can be subjected to secondary ion purification and concentration steps to prepare a fructose raw material having a desired fructose content.

The concentration step included in the fructose production process of the present disclosure is performed by various methods so that the fructose content is 85 wt % or more.

For example, a fructose fraction obtained by a simulated moving bed (SMD) separation method, which has, for example, 20 to 30 wt % of the solid content, may be concentrated to 45 to 55 wt % of the solid content through a concentration step. The step of concentrating in the fructose production process may include concentrating at a temperature of 70 to 85° C. for 10 to 15 minutes. The concentration may be performed under reduced pressure or vacuum conditions using a falling film evaporator or a thin film evaporator. The step of concentrating in the fructose production process may include concentrating at a temperature of 70 to 85° C. for 10 to 15 minutes.

(3) Step of Obtaining an Allulose-Containing Product Using a Fructose Solution In the method for producing allulose according to the present disclosure, a high-purity fructose solution obtained by separating fructose from invert sugar syrup from raw sugar is used as a substrate for the allulose conversion reaction.

In one embodiment, the method for producing allulose includes (1) an allulose conversion step of preparing an allulose conversion product with a fructose-containing raw material; and (2) an allulose separation step of performing separation of the allulose conversion product using ion purification and simulated moving bed (SMB) chromatography to obtain an allulose fraction and fructose raffinate. The method for producing allulose may further include (3) an allulose crystallization step of subjecting the allulose fraction obtained in the separation step of allulose production to ion purification, concentration and crystallization.

In the allulose production process of the present disclosure, both a continuous process and a batch process may be used, and according to an embodiment, a continuous process may be used, but is not limited thereto.

The final product obtained in the fructose separation step according to the present disclosure is subjected to the allulose production process as a raw reaction material for the allulose conversion reaction. The fructose content of the fructose fraction obtained through the high-purity separation step may be 85 wt % or more, and the fructose content of the final product obtained through the concentration step may be 85 to 95 wt % or 85 to 99 wt %. The fructose raw material subjected to the allulose conversion reaction has a fructose content of 85 wt % or more, for example, 85 wt % to 99 wt %, and a monosaccharide and disaccharide content of 5 wt % or less, for example, 1 wt % to 5 wt %. In a specific embodiment, when considering 2 Brix (20 g/L) in HPLC analysis measurement, it is 10 g/L based on glucose (50%), and HMF can be confirmed as 0.05 wt % when set based on 0.01 g/L.

According to the present disclosure, by using a fructose-containing raw material obtained from raw sugar as a raw material substrate for the allulose conversion step, the production yield of allulose can be maximised and the production cost of allulose can be reduced. Further, in the allulose production process, by preparing a fructose-containing raw material directly from raw sugar, a additional separate sugar production process and a sugar decomposition treatment device are not required in the conventional method for producing a fructose-containing raw material using sugar, which is advantageous in the process design and operation.

In one embodiment, the method for producing allulose includes an allulose conversion step of preparing an allulose conversion product from a fructose-containing raw material, and an allulose separation step of performing separation of the allulose conversion product using ion purification and simulated moving bed (SMB) chromatography to obtain an allulose fraction and raffinate. The allulose production process of the present disclosure can use both continuous and batch processes, and according to an embodiment, a continuous process may be used, but is not limited thereto.

The allulose conversion step is a step of performing an allulose conversion reaction to convert a fructose-containing raw material to allulose, and obtains a reaction solution containing allulose converted from fructose as a product of the process.

In one embodiment of the present disclosure, the method for producing allulose according to the biological method includes culturing a strain producing an allulose epimerase or a recombinant strain introduced by a gene encoding an allulose epimerase, and reacting the obtained allulose epimerase with a fructose-containing raw material. The allulose epimerase may be used for a liquid phase reaction or a solid phase reaction using an immobilised enzyme.

Also, allulose may be prepared by reacting a fructose-containing raw material with a composition for production of allulose comprising at least one selected from the group consisting of microbial cells of a strain, a culture of the strain, a lysate of the strain, and an extract of the lysate or culture, after obtaining a strain producing an allulose epimerase or a recombinant strain introduced by a gene encoding an allulose epimerase. When allulose is produced by using the microbial cells of the strain producing the allulose epimerase, it may be carried out in a liquid phase reaction or a solid phase reaction using immobilized cells.

In a specific embodiment of the present disclosure, the strain producing allulose epimerase can convert allulose from fructose in high yield while having high stability or may be a strain capable of producing allulose epimerase. The strain may be a non-GMO strain that is isolated from nature or a mutant strain thereof, or a recombinant strain in which a gene encoding an allulose epimerase is introduced into a host cell. In one embodiment of the present disclosure various strains known as the non-GMO strain may be used. The recombinant strain may include various host cells, such as *Escherichia coli, Bacillus* sp. strain, *Salmonella* sp. strain and *Corynebacterium* sp. strain, and the like. Preferably, it may be a *Corynebacterium* sp. Strain, GRAS strain, and may be *Corynebacterium glutaricum*.

The allulose conversion step according to an embodiment of the present disclosure is performed by a biological method. For example, in the case of a solid phase reaction, the method may further include a step of immobilizing the allulose epimerase or cells on a support and filling the column, and a step of feeding a fructose solution to the filled column. The column to be filled with the support on which the enzyme or cells are immobilized and the method for filling the column can be easily selected by those skilled in the art, depending on the enzyme or cell or immobilization carrier used. In one embodiment of the present disclosure, a packed-bed column can be prepared by filling the column with the immobilized enzyme or cells. An enzymatic reaction, i.e., conversion of fructose to allulose, can be carried out by feeding a solution of fructose as a substrate to the packed-bed column.

In the conversion reaction of allulose, one example of a method for preventing or reducing impurity production in order to prevent or reduce the production of impurities may be a method of performing the allulose production process at a pH of 4 or more and/or a temperature of 70° C. or less. Specifically, the reaction can be carried out under conditions of pH 4.5 to 7.5, for example, pH 4.7 to 7.0, or pH 5.0 to 6.0 or pH 5.0 to 5.5. Further, the reaction may be carried out under a temperature condition of 30° C. or more, for example, 40° C. or more. Since the activation of the enzyme (e.g., epimerase) that converts the fructose into allulose can be regulated by metal ions, the addition of metal ions in the production of allulose may increase the conversion efficiency of fructose to allulose, that is, the allulose production rate. Therefore, the composition for producing allulose may further include one or more metal ions selected from the group consisting of copper ions, manganese ions, calcium ions, magnesium ions, zinc ions, nickel ions, cobalt ions, iron ions, aluminum ions, and the like.

Detailed description of allulose and its production method is described in KR.2014-0021974A, KR2014-0054997A, KR2014-0080282A, or KR 10-1318422B.

The fructose raw material put into the allulose conversion step according to the present disclosure may be prepared by a biological method or a chemical method, or preferably a biological method. The fructose raw material can be prepared by hydrolyzing raw sugar biologically or chemically to prepare a syrup containing glucose and fructose, and separating fructose, to be input as a fructose raw material for the allulose conversion step.

In the allulose production method, the concentration of fructose used as a substrate for efficient allulose production may be 85 w/v % or more, 90 w/v % or more, or 95 w/v % or more, for example 85 to 99w/v %, 88 to 99 w/v %, 88 to 99 w/v %, 85 to 87% (w/v), 88 to 90% (w/v), 91 to 93% (w/v), 94 to 99% (w/v) or 97 to 99% (w/v), based on the total reactants. The concentration of fructose can be determined in consideration of the economic efficiency of the process and the solubility of fructose, and the fructose may be used in the form of a solution dissolved in a buffer solution or water (e.g., distilled water).

(4) Step of Obtaining High-Purity Allulose from the Allulose-Containing Product (Separation Step of the Allulose Conversion Product)

The product obtained in the allulose conversion step in an embodiment of the present disclosure, is a mixture containing fructose as a raw substrate material and allulose as a reaction product, and undergoes a high-purity separation step to obtain an allulose fraction having an increased content of allulose as a target substance and a residual liquid. Since the residual liquid contains a large amount of fructose, which is a substrate for the allulose conversion reaction, it may refer to a fructose raffinate.

The allulose production process according to the present disclosure may include a separation step for the allulose conversion product including ion purification and a simulated moving bed (SMB) chromatographic separation step of the allulose conversion product. In a specific embodiment, the allulose conversion product is subjected to SMB chromatography separation to separate an allulose fraction having a higher allulose content than the allulose conversion product and fructose raffinate, and the allulose fraction is put into an allulose concentration process or crystallization process, and fructose raffinate is put into the fructose production process and recirculated.

The content of allulose in the allulose fraction may include separating/purifying so that it is 85 wt % or more, for example, 85% to 95% (w/w) or more.

The ion purification step in the allulose production process, is a step of removing ions contained in the reaction product, and can be performed before and/or after the SMB chromatography separation step. The primary ion purification in which the ion purification step is performed before the SMB chromatographic separation may be performed in the same or different method as the secondary ion purification of the allulose fraction, and for example, can be carried out by using one or two or more separation columns filled with the same or different types of ion exchange resins. The ion purification step can be performed at a temperature of 35 to 50° C., for example, 38 to 58° C., in consideration of the physical properties of the resin used for ion purification, and ion purification efficiency.

In one embodiment of the present disclosure, before performing the primary ion purification step of the allulose conversion product, a step of treating the allulose conversion reactant with activated carbon may be further performed optionally. The activated carbon treatment is to absorb and remove high molecular or low molecular organic substances, colored ionic substances or proteins that may act as impurities or induce denaturation of allulose. The activated carbon used in the activated carbon treatment step may be coal-based or wood-based, and impurities may be selectively removed depending on the pore size of the activated carbon. In the activated carbon treatment step, the activated carbon is contacted with an allulose solution and reacted at a temperature of 40 to 50° C. for 0.5 to 5 hours, and then the reaction solution including the activated carbon is subjected to a solid-liquid separation step to obtain a filtrate, and impurities may be removed as a filtration residue. The filtration may be performed using a filtration device such as a filter press, In an embodiment of the present disclosure, the high-purity separation step using SMB chromatography is a separation method in which there is no phase change in the separation process and it is easy to secure the stability of the substance. Among these adsorption separation methods, a chromatography separation method is widely used as a liquid phase absorption separation method. Among them, the simulated moving bed (SMB) adsorption separation method is a separation technology proposed in U.S. Pat. No. 2,985,589 in 1961. This method has advantages in that purity and productivity are superior to that of conventional batch chromatography, and the use of a small amount of solvent is possible by continuous separation using a plurality of columns. The simulated moving bed (SMB) adsorption separation step is a step in which the injection of the mixture to be separated and the production of raffinate and extract are continuously performed.

The basic principle of SMB is to simulate the counter-current flow of the stationary phase and the mobile phase by moving the positions between the columns at regular time intervals, thus enabling continuous separation. Because the affinity with the adsorbent is weak, the fast-moving material moves in the direction of the flow of the liquid phase and collects into the extract. Substances that have a weak affinity for the adsorbent and move fast move in the flow direction of the liquid phase and gather in the extract, and substances that have a strong affinity for the adsorbent and move slowly move in the flow direction of the stationary phase and gather in the raffinate. The columns are continuously connected, and the inlet consists of the mixture and mobile phase, and the outlet consists of the target extract and raffinate.

The salt-added strong acid cation exchange resin, which is widely used in the monosaccharide separation step, is used as the separation resin in the SMB. Thus, the product obtained after performing the separation process contains metal ions. Examples of the strong acid cation exchange resin may be a cation exchange resin to which a calcium active group is attached.

FIG. 1 shows a process diagram of a typical simulated moving bed (SMB) adsorptive separation device. A typical simulated moving bed (SMB) adsorptive separation device includes four sections consisting of one or more columns and a desorbent inflow port located between each section, a strong adsorbate extract outlet port, a feed inlet port to be separated and a weak adsorbate raffinate exhaust port. The method for separating a mixture using the simulated moving bed (SMB) adsorption separation device can be applied to a separation step of a mixture of aromatic hydrocarbons, a separation step of ethylbenzene, a separation step of chiral compounds, and the like. It can be applied to the separation step of racemic mixed drugs, which are a final product or an intermediate during the drug manufacturing process.

The high-purity separation step may be performed at a temperature of 45 to 70° C., for example, 50 to 65° C.

(5) Step of Concentrating or Crystalizing Allulose

In the allulose production process of the present disclosure, the allulose fraction obtained in the high-purity separation step using SMB chromatography goes through an allulose concentration step to be commercialized as a liquid syrup, or goes through an allulose crystallization step to be commercialized as an allulose crystals.

This is a step of preparing a concentrate obtained by ion-purifying and concentrating the allulose fraction obtained in the SMB chromatographic separation step in step (4). The concentrate may be used as an allulose syrup product, or can be put into a crystallization process to produce into allulose crystals.

In one embodiment of the present disclosure, the allulose fraction obtained in the high-purity separation step using the SMB chromatography can be subjected to a secondary ion purification step, which may be performed in the same or different method as the primary ion purification performed in the separation step.

The allulose content in the allulose solution to obtain allulose crystals should be in a high concentration in a supersaturated state, but since the content of allulose in the allulose conversion product is low, crystallization cannot be performed directly. Prior to the crystallization step, a step of purifying allulose to increase the content and concentrating it to a desired level should be performed.

In one embodiment of the present disclosure, the step of concentrating the purified allulose solution may be performed at a temperature of 40 to 75° C. or 55 to 75° C. When the temperature of the concentrate is higher than 75° C., thermal denaturation of D-allulose may occur, and when the temperature of the concentrate is lower than 40° C., it is difficult to achieve the desired level of concentration. As the concentration proceeds, the temperature of the reactants increases sharply due to the heat of evaporation, and thus, it is necessary to quickly concentrate while maintaining the temperature of the concentrate at 75° C. or lower.

In one embodiment of the present disclosure, in order to achieve thermal denaturation of allulose and a desired level of concentration, it can be concentrated at a temperature of 55 to 75° C., preferably in the range of 60 to 70° C. The concentration step can be repeated once or twice or more until a desired concentration level is achieved.

Specifically, the concentration step of the allulose fraction obtained in the SMB chromatography separation step can be performed by various methods, and the solid content of the concentrate can be made to be 70 brix or more. For example, the allulose fraction (e.g., solid content of 20 to 30 wt %) obtained by the simulated moving bed adsorptive separation method may be concentrated to a solid content of 70 brix or more through a concentration step. The solid content of the allulose concentrate may be 70 brix or more, for example, 70 brix to 85 brix. In order to prevent or reduce the formation of impurities, the concentration step may be performed on the allulose fraction obtained in the SMB chromatography separation step under temperature conditions of 40 to 70° C. or lower, and optionally, the concentration step can be performed by dividing it into at least two steps or more. For example, when the concentration step is divided into two steps, the allulose syrup is subjected to a primary concentration so as to have a concentration of 30 to 50 bx, and the primary concentrate can be again subjected to a secondary concentration so as to have a concentration of 60 to 85 bx.

The step of concentrating in the allulose production process may include concentrating at a temperature range of 55 to 75° C. for 10 to 15 minutes. The concentration may be performed under reduced pressure or vacuum conditions using a falling film evaporator or a thin film evaporator.

The allulose content the allulose concentrate is almost unchanged from the allulose content in the allulose fraction obtained in the SMB chromatography separation step, and the solid content is increased so that a subsequent crystallization step can be performed. The allulose content in the allulose concentrate is 94 wt % or more, 95 wt % or more, 96 wt % or more, 97 wt % or more, 98 wt % or more, or 99 wt % or more based on 100 wt % of the total solid content.

The allulose crystallization includes a step of performing a secondary ion purification for the allulose fraction obtained in the high-purity separation step, a step of concentrating the ion-purified allulose fraction, and a step of crystallizing allulose from the concentrate to obtain allulose crystals and an allulose crystallization mother liquor. A specific example of the allulose separation step may include primary ion purification, high-purity chromatography separation, secondary ion purification, concentration and crystallization steps, and optionally, the allulose conversion product may be subjected to a desalting step, a decolorizing process, or a decolorizing and desalting step.

The content of allulose in the allulose fraction may include separating/purifying so that it is 85 wt % or more, 90 wt % or more, 91 wt % or more, 92 wt % or more, 93 wt % or more, 94 wt % or more, or 95 wt % or more, for example 85% to 99.9% (w/w) or more.

Allulose contained in the allulose crystal has a purity of 90 wt % or more, 95 wt % or more, or 99 wt % or more, and the allulose content in the crystallization mother liquor may be 85 wt % or more, 90 wt % or more, 93 wt % or more, or 95 wt % or more, for example, 85 wt % to 95 wt %.

Allulose obtained by the method of the present disclosure can be purified and/or crystallized by a conventional method, and such purification and crystallization belong to the technique that is common to those skilled in the art. For example, it may be achieved by one or more methods selected from the group consisting of centrifugation, filtration, crystallization, ion exchange chromatography, and combinations thereof.

In one embodiment, the allulose fraction obtained in the high-purity separation step using the SMB chromatography can be subjected to a secondary ion purification, which can be performed by the same or different method as the primary ion purification used in the separation step of allulose.

The method for preparing D-allulose crystals according to the present disclosure include concentrating the purified D-allulose solution. The content of allulose in the allulose solution for obtaining allulose crystals should be 70 wt % or more. Since the purity of allulose in the allulose solution prepared by the allulose epimerase is as low as 20 to 30 wt %, direct crystallization cannot be performed, and allulose must be purified and concentrated to the desired level before the crystallization step. In one embodiment of the present disclosure, in order to achieve thermal denaturation of allulose and a desired level of concentration, it can be concentrated at a temperature ranging from 55 to 75° C. The concentration step can be repeated once or twice or more until a desired concentration level is achieved.

The cooling and crystallization step may include rapidly cooling to a temperature range of 10 to 25° C. through a heat exchanger, and then repeatedly performing temperature increase and cooling to induce crystal growth.

The method for producing D-allulose crystals according to the present disclosure may further include a step of recovering the allulose crystals obtained in the crystallization step by centrifugation, washing with deionized water, and the drying the crystals.

An embodiment according to the present disclosure relates to an allulose production device that includes an allulose conversion reactor for performing an allulose conversion reaction from a fructose raw material using a biological catalyst, a column filled with an active group-attached cation exchange resin, and also includes a simulated moving bed (SMB) chromatographic separator having an inlet for raw material and an outlet for discharging the allulose fraction and fructose raffinate.

The fructose separation device includes an ion purifier having a column filled with an ion exchange resin for ion purification of an invert reaction product, and a column filled with a cation exchange resin to which an active group is attached, and may include a simulated moving bed (SMB) chromatography separator having an inlet for introducing the reactants that have passed through the ion purifier and an outlet for discharging a fructose fraction and raffinate, a concentrator for concentrating the fructose fraction discharged from the separator, and a connection unit that connects the high-purity fructose liquid production device and the allulose production device for providing die fructose-containing raw material discharged from the concentrator to the allulose production device.

Advantageous Effects

The method for producing allulose according to the present disclosure can simplify the production process by eliminating a sugar production process and a glucose production process, as compared with a conventional method of producing allulose using sugar or isomerized fructose obtained from starch, reduce production cost by utilizing low-cost raw materials, and control the content of impurities contained in allulose syrup or powder by reducing the content of oligosaccharides having DP3 or higher and other impurities contained in isomerized sugar syrup using a conventional starch in a conventional method, and a device used therefor.

BRIEF DESCRIPTION OF THE DRAWINGS

FIG. 3 is HPLC analysis results of samples obtained in a sugar production process using raw sugar, where each sample is a raw sugar solution and a crystallization mother liquid for sugar production.

DETAILED DESCRIPTION OF THE EMBODIMENTS

Figure 1:
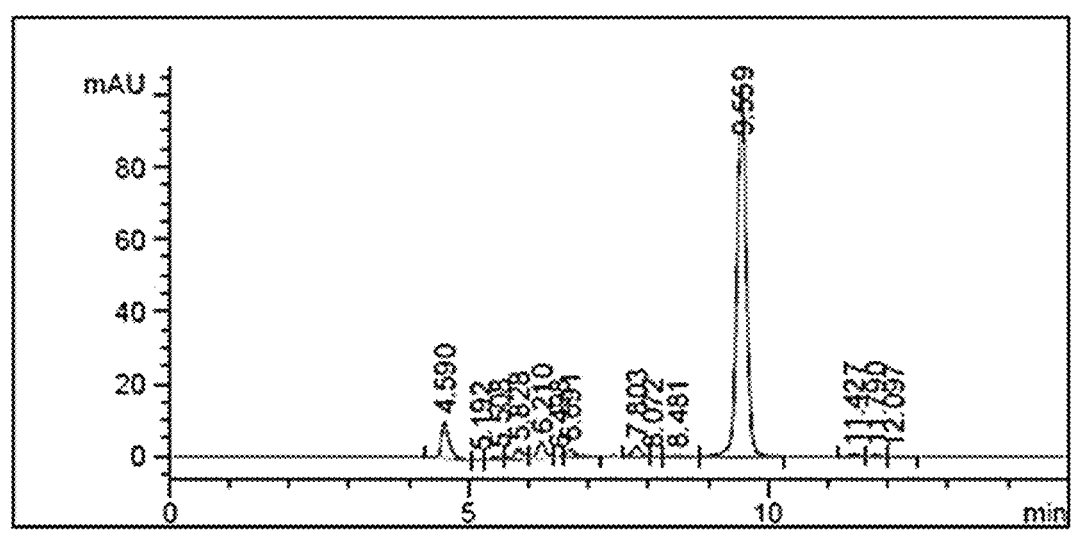
FIG. 1 is an HPLC analysis result of an allulose conversion product prepared using raw sugar-derived fructose according to an embodiment of the present disclosure.

The present disclosure will be described in more detail with reference to the following examples, but these examples are for illustrative purposes only and are not intended to limit the scope of the present disclosure.

Example 1: Production of Allulose Using Raw Materials for Sugar Production 220 kg of raw sugar and 180 kg of distilled water were mixed, and the mixture was adjusted to pH 4.12 with 1N HCl to prepare a reaction solution having a solid content of 55 Brix. The reaction solution was treated with 0.1 wt % of invertase (Sumizyme INV-L, Ockzone Biochem) under temperature conditions, and the treated solution was reacted for 24 hours to obtain a reaction product solution containing 50.0 wt % of glucose and 48.6 wt % of fructose. The raw sugar was prepared from sugar cane, and has a sugar content of 98.5%.

The reaction product solution was treated with 1.0 wt % of activated carbon at a temperature of 80° C., and decolorized for 30 minutes, and the activated carbon was filtered to perform discoloration treatment. The decolorization-treated reaction product solution was flown through a cation exchange resin (SCRB), an anion exchange resin (AMP24), and a mixed resin (MB) of cation and anion exchange resins at a rate of twice the volume of the ion exchange resin per hour, thereby removing impurities such as colored and ionic components. The product from which the impurities were removed was subjected to a high-purity separation process (SMB) for fructose fractionation using a chromatography filled with a calcium ($Ca^{2+}$) type ion exchange resin. Thereby, a fructose fraction having a fructose content of 85 wt % in the solid content was obtained. The fructose fraction was concentrated to obtain a fructose solution having a solid content of 50 wt % and a fructose content of 98.1 wt %.

Allulose was prepared using the prepared fructose raw material. Specifically, the allulose conversion step and the separation step were performed using the prepared fructose solution having a solid content of 50 wt % and a fructose content of 98.1 wt % at a flow rate of 3.8 m3/hr. The allulose content of the reactant obtained through the allulose conversion step was 20 to 23 wt %, and after ion purification, it was flowed through a separation step at a concentration of 45 to 50 wt %. Raffinate generated during separation using Ca+ type separation (SMB) resin was generated by 3 m3 per hour.

In the allulose conversion step, a fructose solution was flown through a column in which an allulose enzyme was immobilized to obtain a low-purity allulose having an allulose content of 21.8 wt %. Specifically, the allulose syrup was prepared from a fructose substrate by a biological method according to the production method as described in KR 10-1318422B.

Then, low-purity allulose was flown through an anion exchange resin and a mixed resin of cation and anion exchange resins to obtain a low-purity allulose that has flown through the ion resin. With respect to the low-purity allulose flown through the resin, a high-purity allulose fraction was separated using chromatography filled with a calcium ($Ca^{2+}$) type ion exchange resin to prepare a high-purity allulose with an allulose content of 95 wt % or more. The high-purity allulose was flown through an anion exchange resin and a mixed resin of cation and anion exchange resins to obtain an ion-purified high-purity allulose. The obtained ion-purified high-purity allulose was concentrated to prepare a high-purity allulose concentrate having a solid content of 72 brix and a purity of 98.5 wt %.

Comparative Example 1: Production of Starch-Derived Allulose and Analysis of 5-HMF Content In the method for producing allulose syrup in this Comparative Example, the allulose conversion step and the separation step of Example 1 were substantially performed, but as a substrate for the allulose conversion reaction, the starch-derived fructose raw material containing 90 wt % of fructose was reacted with 50 mM PIPES buffer solution under the conditions of pH 7.5 and 60° C. to obtain an allulose concentrate having a solid content 72 brix and an allulose purity of 97.5 wt %.

The starch-derived fructose was mixed with water so that the amount of corn starch was 30 to 35 wt %, and then subjected to enzyme hydrolysis to obtain a saccharified solution having glucose content of 88 wt % or more. Then, the saccharified solution was subjected to vacuum drum filtration to remove insoluble substances. Thereby, a fructose isomerization product (fructose content 42 wt % syrup) was obtained. The reaction product (fructose content 42 wt % syrup) that has subjected to the fructose isomerization step was flown through the first ion purification step consisting of a strong acid resin, a weak basic resin, and a strongly acidic resin and a weakly basic mixed resin, and the concentrated to 50 wt % of solids via ion purification, and then passed through SMB chromatography step. The fructose fraction was subjected to secondary ion purification and concentration steps to obtain a fructose-containing raw material solution having a solid content of 50 Brix and a fructose content of 90 wt %.

Using the fructose-containing solution, an allulose conversion product was prepared in substantially the same manner as in the allulose production process of Example 1. The ion purification, separation step using Ca+ type separation (SMB) resin, ion purification, and concentration process were performed to produce allulose. The final obtained allulose solution was prepared as a high-purity allulose concentrate having a solid content of 72 Brix and an allulose purity of up to 99 wt % (95 to 99wt % in the process).

Test Example 1: Analysis of 5-HMF Content of Allulose Derived from Raw Materials for Sugar Production

(1) Preparation of Analysis Samples

Two samples were prepared, including a high-purity fructose solution (sample 1), which is a raw material substrate for allulose production prepared in Example 1, and a high-purity allulose (sample 2) that has undergone a concentration process, and diluted to 5 Brix by adding purified water to prepare an analysis sample for 5-HMF analysis.

(2) Analysis Using a Spectrophotometer

As a method for measuring 5-HMF content using a spectrophotometer, the analysis sample was placed in a 1 ml quartz cuvette, measured with a spectrophotometer at absorbance at 280 nm and absorbance at 250 nm, and calculated according to Equation 1 to obtain 5-HMF content in the sample. Measurement result of 5-HMF content using the spectrophotometer and the measurement results of 5-HMF content using HPLC analysis are shown in Table 1 below. In Equation 1, A (280 nm) and A (250 nm) are absorbance values measured at 280 nm or 250 nm, respectively. The measurement results of 5-HMF content using the spectrophotometer are shown in Table 1 below.

$$HMF(\text{mg}/L) = \frac{\{(A(280\,\text{nm}) - A(250\,\text{nm})) - 0.00149\}}{0.0923} \qquad \text{[Equation 1]}$$

According to the measurement result of 5-HMF content using the spectrophotometer in Table 1 below, Sample 1 of Example 1, in which fructose, a substrate of the allulose conversion reaction, was prepared from raw sugar, had an HMF content of 0.53 (mg/L). Starch-derived fructose (Comparative sample 1) according to Comparative Example 1 in Table 2 below was analyzed spectrophotometrically. As a result, considering that the content of HMF was 2.29 (mg/L), it was confirmed that the HMF content of the raw sugar-derived fructose substrate of Example 1 was very low.

Samples 1 and 2 according to Example 1 showed a remarkable difference in HMF content from Comparative samples 1 and 2 according to Comparative Example 1. Therefore, it could be confirmed that according to this Example, the fructose-containing raw material derived from the raw material for sugar production and the allulose syrup prepared using the same only have a difference in 5-HMF content in fructose-containing raw materials, but also has a difference in HMF content in produced and separated allulose syrup, as compared with starch-derived fructose-containing raw materials and allulose syrup produced using them, and that it maintained a remarkably lower state than Comparative Example.

(3) HPLC Analysis

As an analysis method of 5-HMF content using HPLC analysis, specifically, as the HPLC-UV analysis conditions for the prepared analytical sample, the analysis was performed at 30° C. using a C18 (Shiseido, Capcell pak 4.6 mm Φ×250 mm) column, while flowing 90% (v/v) of water and 10% (v/v) of methanol as the mobile phase at a flow rate of 0.6 ml/min, and it was analyzed using a UV Detector. The sample analysis result using the HPLC analysis shows the area of each peak in the HPLC result graph in Table 1 below, and the relative content of the C18 compound (HMF) contained in each sample can be confirmed by using the peak area of the C18 compound (5-HMF) by HPLC analysis.

TABLE 1

| Sample | A280 nm | A250 nm | Spectrophotometric analysis HMF(mg/L) | C18 area by HPLC analysis |
|---|---|---|---|---|
| Sample 1 | 0.151 | 0.101 | 0.53 | * |
| Sample 2 | 0.452 | 0.226 | 1.24 | 83.6 |

It was confirmed that the content of 5-HMF in the sample obtained in the allulose production process using raw sugar was lower as compared with a comparative sample obtained in the allulose production process using starch-derived fructose. Therefore, it was confirmed that the product according to Example 1 had a higher allulose purity. Considering the C18 area by HPLC analysis in Table 1, it was confirmed that the difference from the HMF content conducted in Test Example 2 is significantly large. It was confirmed that when measured on samples of the same solid content, the peak of HMF is high, and when compared based on the area, the starch-derived allulose slightly increases in the amount of HMF. Especially when checking the sample 2 and the Comparative sample 2 that have completed the final concentration step, it was confirmed that the area value had a large difference.

Therefore, in the production of raw sugar-derived allulose, it is possible to produce high-purity allulose with higher purity and fewer by-products than conventional starch-derived allulose.

Test Example 2: Analysis of By-Product Content of Starch-Derived Allulose

(1) Preparation of Analytical Sample's

For the allulose prepared in Comparative Example 1, two types of samples were obtained for each process in the same manner as the sample of Test Example 1, and diluted to 5 brix by adding purified water to prepare an analytical sample.

Specifically, in the process for producing allulose, two sample groups were collected including high-purity starch-free high-purity fructose solution (Comparative sample 1) and concentrated high-purity allulose (Comparative sample 2) as the raw material substrate, and diluted to 5 brix for 5-HMF analysis to prepare an analytical sample.

(2) Analysis Using a Spectrophotometer

The analytical sample was analyzed in substantially the same manner as the measuring method of 5-HMF content using a spectrophotometer according to Test Example 1. The measurement results of 5-HMF content using the spectrophotometer are shown in Table 2 below.

It was confirmed that there was a significant difference in HMF content between raw sugar-derived fructose-containing raw materials and starch-derived fructose-containing raw materials. When starch-derived allulose is produced, the number of manufacturing steps increases as compared with raw sugar-derived allulose, and the amount of HMF becomes higher than that of raw sugar-derived allulose. In this example, comparing Comparative sample 2 and sample 2, it can be confirmed that there is a difference in the amount of final HMF, and raw sugar-derived allulose is higher even in the purity of the final allulose.

Therefore, in the production of raw sugar-derived allulose, it was confirmed that high-purity allulose with high purity and few by-products can be produced as compared with allulose made from starch.

(3) HPLC Analysis

The analytical sample was analyzed in substantially the same manner as the analysis method for 5-HMF content using HPLC analysis according to Test Example 1. As for the sample analysis result using the above HPLC analysis, the area of each peak in the HPLC result graph is shown in Table 2 below.

TABLE 2

| Sample | A280 nm | A250 nm | Spectrophotometric analysis HMF(mg/L) | C18 area by HPLC analysis |
|---|---|---|---|---|
| Comparative sample 1 | 2.359 | 2.146 | 2.29 | * |
| Comparative sample 2 | 0.767 | 0.227 | 5.83 | 136.8 |

HMF can be measured with UV Detector using HPLC. In order to compare the relative difference between HMF of raw sugar-derived allulose and starch-derived allulose, HPLC was measured by setting the same concentration. As a result, when sample 6 and Comparative sample 6 are confirmed, it is possible to confirm the difference in area. Further, it can be confirmed that the amount of HMF is proportional to the area, but the amount of HMF in raw sugar-derived allulose is small.

Test Example 3: Analysis of the By-Products Contents in Allulose Products for each Production Step A fructose solution, which is a raw material substrate for allulose production prepared in Example 1, was obtained. As the fructose solution, a fructose solution having a solid content of 50 Brix and a fructose content of 98.1 wt % was used for analysis as sample 6-1. The allulose conversion product obtained by the allulose conversion step using the fructose solution was used as sample 6-2, the purified product in which the allulose conversion product was subjected to ion purification was used as sample 6-3, the allulose fraction obtained by separating the purified product subjected to ion purification using a $Ca^{2+}$ type separation (SMB) resin was used as sample 6-4, the purified product obtained by purifying the allulose fraction was used as sample 6-5, and a high-purity allulose concentrate having a purity of 98.5 wt % with a solid content of 72 Brix obtained by concentrating the purified product was used as sample 6-6.

A starch-derived fructose solution, which is a raw material substrate for allulose production, was obtained according to Comparative Example 1. As the fructose solution, a fructose solution having a solid content of 50 Brix and a fructose content of 90 wt % was used as a Comparative sample 6-1 for analysis. The allulose conversion product obtained by the allulose conversion step using the fructose solution was used as a Comparative sample 6-2, the purified product obtained by ion-purifying the allulose conversion product was used as a Comparative sample 6-3, the allulose fraction obtained by separating the purified product subjected to ion purification using a Ca+ type separation (SMB) resin was used as a Comparative sample 6-4, the purified product obtained by purifying the allulose fraction was used as Comparative sample 6-5, and a high-purity allulose concentrate having a solid content of 72 Brix and a purity of 95 wt % obtained by concentrating the purified product watts used as a Comparative sample 6-6.

Figure 4:
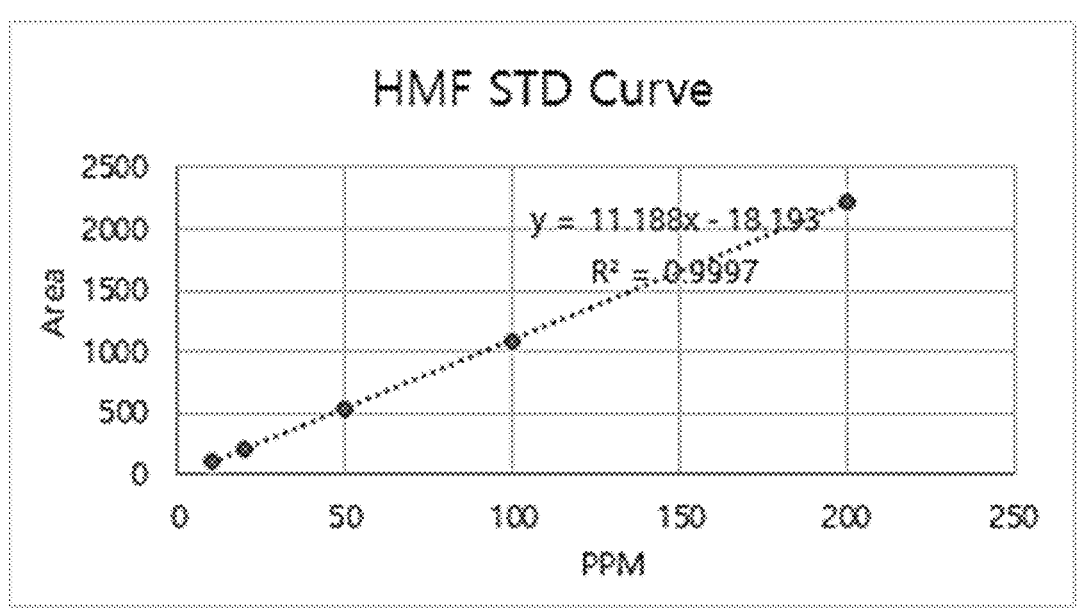
FIG. 4 shows a standard curve for HMF content analysis using HPLC for starch-derived allulose and raw sugar-derived allulose solutions.

Purified water was added to the prepared samples 6-1 to 6-6 and Comparative samples 6-1 to 6-6 and diluted with 5 Brix to prepare an analytical sample for 5-HMF analysis. The 5-HMF analysis method was performed by HPLC analysis in substantially the same manner as the 5-HMF content analysis method in the sample of Test Example 1, and the analysis results are shown in Table 3 below. In Table 3 below, the amount of change (percentagae) is expressed as a percentage of the relative content of HMF included in each sample based on the HMF content included in the raw material sample 6-1 or Comparative sample 6-1. The standard curve used for the HPLC analysis is shown in FIG. 4.

TABLE 3

| Sample | ppm | Changed amount(%) based on raw material |
|---|---|---|
| sample 6-1 | 4.36 | 100% |
| sample 6-2 | 137.97 | 3085% |
| sample 6-3 | 4.25 | 18% |
| sample 6-4 | 17.03 | 311% |
| sample 6-5 | 7.96 | 103% |
| sample 6-6 | 8.37 | 113% |
| Comparative sample 6-1 | 16.4 | 100% |
| Comparative sample 6-2 | 110.9 | 576% |
| Comparative sample 6-3 | 42.1 | 157% |
| Comparative sample 6-4 | 82.1 | 401% |
| Comparative sample 6-5 | 63.7 | 288% |
| Comparative sample 6-6 | 46.0 | 180% |

In Table 3, the content of 5-HMF in the sample obtained in the allulose production process using raw sugar, and the content of 5-HMF in the sample obtained in the allulose production process using starch was measured for each sample collected by each production process. According to the results of Table 3, it can be understood that the content of HMF does not depend on the raw material, but rather the content of by-products of the final product increases according to the process at the time of producing the product. In one example, reviewing Table 3, it is possible to confirm the difference in the HMF content of the product compared to the HMF content of the raw material high fructose. Therefore, it is possible to reduce the content of by-products at the time of producing raw sugar-derived allulose.

Test Example 4: Analysis of Storage Stability of Allulose Products

The high-purity allulose produced in Example 1 and Comparative Example 1 was used as a sample. Specifically, the final allulose solutions prepared in Example 1 and Comparative Example 1 were adjusted to a solid content of 70 Brix and pH 4, 5, 6, and 7 to prepare analytical samples. 10 ml each was taken and used for analysis.

The analytical samples were stored at 70° C. for 24 hours under conditions of pH 4, 5, 6, and 7 and subjected to a severe test. To determine the allulose content and the content of by-products, an HPLC analyzer was used. As the HPLC-UV analysis conditions, the analysis was performed at 30° C. using a C18 (Shiseido, Capcell pak 4.6 mm Φ×250 mm) column, while flowing 90% (v/v) of water and 10% (v/v) of methanol as the mobile phase at a flow rate of 0.6 ml/min, and it was analyzed using a UV Detector. The HPLC analysis results of the sample of Example 1 are shown in Table 1 below, and the HPLC analysis results of the Comparative sample of Comparative Example 1 are shown in Table 2 below.

As shown in the HPLC analysis result graph of FIG. 1, the allulose sample according to Example 1 showed a small decrease in storage conditions as compared with the starch-derived allulose of Comparative Example 1, and increase in the content of the by-product (5-HMF) is also less than that of the starch-derived allulose of Comparative Example 1.

Figure 2:
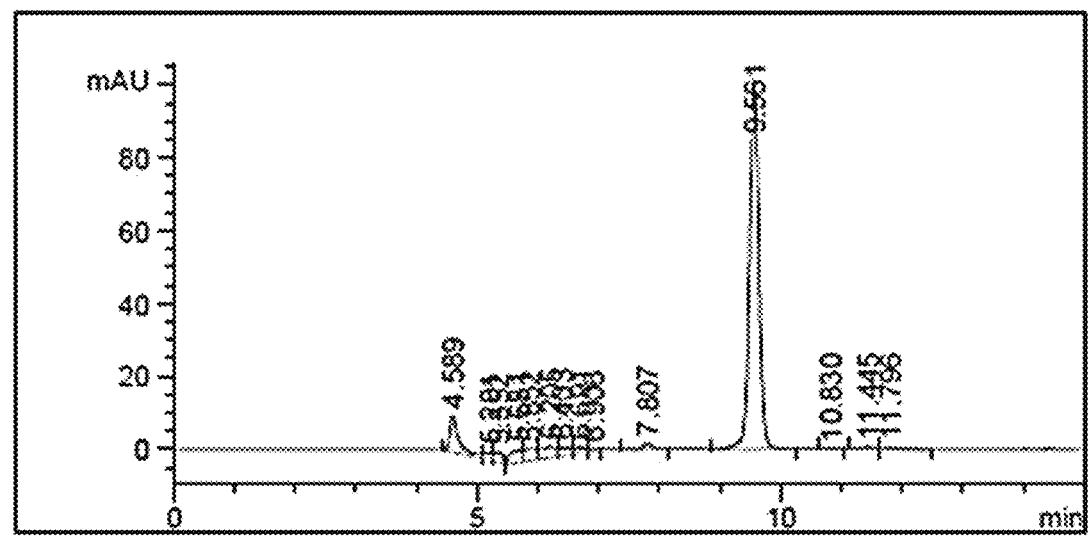
FIG. 2 is an HPLC analysis result of an allulose conversion product prepared using starch-derived fructose according to Comparative Example 1.

As shown in the HPLC analysis result graph of FIG. 2, it was confirmed that on the starch-derived allulose of Comparative Example 1, the decrease in the allulose content and the increase in the by-product (5-HMF) content were significantly higher than those of the raw sugar-derived allulose of Example 1 under the storage condition at 70° C. for 24 hours.

Therefore, it was confirmed that the storage stability of raw sugar-derived allulose is higher than that of starch-derived allulose.

Test Example 5: Analysis of pH Stability of Allulose Products

The high-purity allulose prepared in Example 1 and Comparative Example 1 was used as a sample. Specifically, the final allulose solution prepared in Example I and Comparative Example 1 was adjusted to pH 4, 5, 6, and 7 using 1N HCl and 1N NaOH, and then the solid content was adjusted to 70 Brix, and the pH was adjusted to pH 4, 5, 6, and 7, respectively, to prepare an analytical sample. Each 10 ml of the assay sample was taken and used for the assay.

Then, the analytical sample was stored at 70° C. for 24 hours and subjected to a severe test. Then, the allulose content and the by-product content were analyzed in substantially the same manner as the HPLC analysis method of Test Example 1. The HPLC analysis results for the sample of Example 1 and the sample of Comparative Example 1 are shown in Table 4 below. The allulose content immediately after the preparation of the assay sample was used as a control.

TABLE 4

| Sample | pH condition | Control group | After 24 hours | Reduced amount (wt %) |
|---|---|---|---|---|
| Example 1 | 4 | 98.1 | 92.6 | 5.5 |
| Example 1 | 5 | 98.3 | 95.5 | 2.8 |
| Example 1 | 6 | 98.2 | 96.0 | 2.2 |
| Example 1 | 7 | 98.2 | 96.2 | 2.0 |
| Comparative Example 1 | 4 | 96.7 | 89.9 | 6.8 |
| Comparative Example 1 | 5 | 97.0 | 92.7 | 4.3 |
| Comparative Example 1 | 6 | 96.9 | 92.8 | 4.0 |
| Comparative Example 1 | 7 | 96.9 | 93.3 | 3.6 |

Comparing the results of storage under harsh conditions according to pH conditions for the allulose syrup obtained in Example 1 and Comparative Example 1, it was confirmed that the amount of reduction of raw sugar-derived allulose according to Example 1 is small compared to the starch-derived allulose of Comparative Example 1, and the raw sugar-derived allulose is more preferable in terms of storage stability according to pH conditions.

Test Example 6: Analysis of By-Products for Each Step of Sugar Purification Process Sugar is produced by re-purifying the mother liquor during progress of crystallization in the existing sugar production process. The mother liquid was obtained and the by-products for each process were analyzed under the same conditions as those of Test Example 2 by HPLC method. Specifically, the analysis samples were raw sugar, mother liquid 1, mother liquid 2, mother liquid 3, and mother liquid 4.

Raw sugar was collected and analyzed before entering the existing process, and when this raw sugar was dissolved and crystallized, sugar was released, and the remaining solution is called mother liquor 1. When mother liquor 1 is crystallized again, sugar with a lower quality than the crystallization in the first stage is produced, and the remaining liquid is called mother liquor 2. In this manner, sugar was crystallized two more times, and mother liquid 3 and mother liquid 4 were obtained sequentially. The liquid that remains alter crystallization in the process of crystallizing sugar is called mother liquor. As the crystallization step proceeds, the concentration of impurities in the mother liquor becomes more intense. Therefore, when the existing raw sugar is dissolved and sugar crystallization is promoted, impurities become thick in the mother liquor remaining excluding the sugar obtained as a product.

As a result of analyzing the sample obtained in the sugar production process, many unknown peaks were detected, and these substances are produced as sugar and are discarded in the same way as wastewater, which may cause future environmental problems. When sugar converts to allulose, a large amount of by-products are generated in the process of producing even sugar, which requires a process that has to deal with many by-products before producing allulose.

As shown in FIG. 3, when sugar converts to allulose, a large amount of by-products are generated in the process of producing even sugar, which requires a process to process many by-products until allulose is produced. When allulose is produced directly from raw sugar as in Examples, since it goes directly to allulose without going through this process, it is advantageous because a separate process of generating by-products is eliminated.

The invention claimed is:

1. A method for producing allulose, the method comprising the steps of:
   obtaining an invert sugar syrup containing fructose and glucose by treating a raw material for sucrose production containing sucrose with an invertase, without separating or purifying sucrose crystal from the raw material for sucrose production,
   preparing a fructose-rich feedstock for allulose production by subjecting the invert sugar syrup into a fructose separation process, and
   performing an allulose conversion reaction using the fructose-rich feedstock,
   wherein the raw material for sucrose production is juice or concentrate of sugar cane, juice or concentrate of sugar beet, a crystal obtained by removing molasses from the juice or the concentrate, or a solution of the crystal, and
   wherein the fructose-rich feedstock contains 90 wt % or more fructose based on the total saccharide solid content of the fructose-rich feedstock, wherein the fructose separation process comprises an activated carbon treatment step, an ion purification step, a high-purity separation step using simulated moving bed (SMB) chromatography, and a concentration step for the invert sugar syrup.

2. The method of claim 1, wherein the invert sugar syrup comprises fructose, glucose, and disaccharide or higher saccharide.

3. The method of claim 1, wherein the invert sugar syrup has a saccharide solid content of 10 wt % or more.

4. The method of claim 1, wherein the total content of fructose and glucose is 90 wt % or more, based on the total saccharide solid content of the invert sugar syrup.

5. The method of claim 1, wherein fructose is included in an amount of 40 wt % or more, and glucose is included in an amount of 60 wt % or less, based on 100 wt % of the total solid content of fructose and glucose contained in the invert sugar syrup.

6. The method of claim 1, wherein the fructose-rich feedstock contains 0.001 to 2.2 mg/L of 5-hydromethylfurfural (5-HMF).

7. The method of claim 1, wherein the fructose-rich feedstock has a content of oligosaccharides having degree of polymerization of 3 (DP3) or higher in an amount 2.0 wt % or less based on the solid content.

8. The method of claim 1, wherein the product of the allulose conversion reaction comprises 0.001 to 5.7 mg/L of 5-HMF.

9. The method of claim 1, wherein the raw material for sucrose production is obtained by dissolving a crystal obtained by removing molasses from the juice or the concentrate.

10. The method of claim 1, wherein the invert sugar syrup is obtained by adjusting the raw material for sucrose production to a temperature of 55 to 75° C. and a pH of 4.0 to 5.0, and treating with 0.01% to 1.0 wt % of invertase, based on the solid content of the raw material for sucrose production.

11. The method of claim 1, wherein the product of the allulose conversion reaction is obtained by subjecting the fructose-rich feedstock for allulose production to a biological allulose conversion reaction.

12. The method of claim 11, wherein the allulose conversion reaction uses a biological catalyst having an allulose conversion rate of 15% to 70%.

13. The method of claim 1, which further comprises a step of obtaining allulose crystals and a crystallization mother liquor by concentrating an allulose fraction, and crystallizing allulose from the product of the allulose conversion reaction.

* * * * *